(12) United States Patent
Schulman (10) Patent No.: US 6,516,808 B2
(45) Date of Patent: Feb. 11, 2003

(54) HERMETIC FEEDTHROUGH FOR AN IMPLANTABLE DEVICE

(75) Inventor: Joseph H. Schulman, Santa Clarita, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 8 days.

(21) Appl. No.: 09/882,712

(22) Filed: Jun. 14, 2001

(65) Prior Publication Data

US 2001/0039374 A1 Nov. 8, 2001

Related U.S. Application Data (63) Continuation-in-part of application No. 09/100,310, filed on Jun. 19, 1998, now Pat. No. 6,259,937, which is a continuation-in-part of application No. 08/928,867, filed on Sep. 12, 1997, now Pat. No. 5,999,848.

(51) Int. Cl.[7] ............................. A61B 5/14; A61B 19/02
(52) U.S. Cl. ..................... 128/899; 607/36; 600/323; 600/373; 600/365; 206/438
(58) Field of Search ........................... 607/36; 128/899; 600/347, 323, 325, 327, 365, 372, 373, 309; 206/438; 174/52.4

(56) References Cited

U.S. PATENT DOCUMENTS

| | | | |
|---|---|---|---|
| 3,558,993 A | | 1/1971 | Rigby |
| 4,041,955 A | | 8/1977 | Kelly et al. |
| 4,152,540 A | | 5/1979 | Duncan et al. |
| 4,159,075 A | | 6/1979 | Ljung et al. |
| 4,474,827 A | | 10/1984 | Feralli |
| 4,525,766 A | | 6/1985 | Petersen |
| 4,650,922 A | * | 3/1987 | McPherson ............... 174/52.4 |
| 4,725,480 A | | 2/1988 | Gurol |
| 4,763,188 A | * | 8/1988 | Johnson .................... 174/52.2 |
| 4,837,049 A | * | 6/1989 | Byers et al. ................ 29/829 |
| 4,861,641 A | | 8/1989 | Foster et al. |
| 4,882,298 A | | 11/1989 | Moeller et al. |
| 5,193,539 A | | 3/1993 | Schulman et al. |
| 5,280,413 A | | 1/1994 | Pai |
| 5,293,069 A | | 3/1994 | Kato et al. |
| 5,381,039 A | | 1/1995 | Morrison |
| 5,397,917 A | | 3/1995 | Ommen et al. |
| 5,497,772 A | | 3/1996 | Schulman et al. |
| 5,508,368 A | | 4/1996 | Knapp et al. |
| 5,523,622 A | | 6/1996 | Harada et al. |
| 5,660,163 A | | 8/1997 | Schulman et al. |
| 5,750,926 A | | 5/1998 | Schulman et al. |
| 6,043,437 A | | 3/2000 | Schulman et al. |
| 6,081,736 A | | 6/2000 | Colvin et al. |
| 6,119,028 A | | 9/2000 | Schulman et al. |

FOREIGN PATENT DOCUMENTS

| | | |
|---|---|---|
| EP | 0266210 | 5/1988 |
| FR | 2620275 | 3/1989 |
| WO | WO82/01134 | 4/1982 |
| WO | WO95/34342 | 12/1995 |
| WO | WO97/06853 | 2/1997 |

\* cited by examiner

*Primary Examiner*—Kennedy Schaetzle
(74) *Attorney, Agent, or Firm*—Lee J. Mandell (57) ABSTRACT

The present invention provides an implantable substrate sensor comprising electronic circuitry formed within, or on, a substrate. A protective coating then covers the substrate, forming a hermetically sealed package having the circuitry under the coating. The circuitry has electrically conductive pads for communicating and/or providing power to the circuitry. Electrical pathways provide hermetic electrical connection to the conductive pads for external connection to the sealed circuitry. In a first embodiment, the pathway is a via that is made from a biocompatible material that is made hermetic by either increasing its thickness or by ion beam deposition. Alternatively, the pathways are formed from metal traces, surrounded by a biocompatible insulation material, essentially parallel to the surface of the substrate that are connected to the conductive pads by first vias and have second ends externally accessible to the sealed package to provide external electrical connection to the hermetically sealed circuitry within.

23 Claims, 8 Drawing Sheets

HERMETIC FEEDTHROUGH FOR AN IMPLANTABLE DEVICE

This application is a continuation-in-part of U.S. patent application Ser. No. 09/100,310 filed Jun. 19, 1998, now U.S. Pat. No. 6,259,937, which in turn is a continuation-in-part of U.S. patent application Ser. No. 08/928,867 filed Sep. 12, 1997, now U.S. Pat. No. 5,999,848.

FIELD OF THE INVENTION

The present invention is generally directed to an implantable medical device, e.g., an implantable sensor, and in particular is related to techniques for providing hermetic connections to such a device.

BACKGROUND OF THE INVENTION

The present invention relates to semiconductor substrates, and more particularly to a semiconductor substrate fabricated to include hermetically-sealed electronic circuitry as well as non-hermetically-sealed electrodes thereon so as to form an implantable sensor or other implantable electronic device.

In U.S. Pat. No. 5,660,163 (hereafter the '163 patent), there is disclosed an implantable glucose sensor which is fabricated on a ceramic substrate. Working electrodes and other elements associated with the sensor are exposed to a conductive fluid contained within a reservoir or inner sheath that covers the substrate. An outer sheath is also placed over the sensor, with a window formed over one of the working electrodes. A selected enzyme, such as glucose oxidate (GO), is placed within the window.

As disclosed in the '163 patent, five wires or conductors are attached to the electrodes and connected to electronic circuitry, e.g., a circuit such as is shown in FIG. 3 of the '163 patent. U.S. Pat. No. 5,660,163 is incorporated herein by reference in its entirety.

Additional features, aspects and improvements of a glucose sensor of the type disclosed in the '163 patent are further disclosed in U.S. patent application Ser. No. 08/953,817, filed Oct. 20, 1997, now U.S. Pat. No. 6,081,736; Ser. No. 08/954,166, filed Oct. 20, 1997, now U.S. Pat. No. 6,119,028; and Ser. No. 08/928,867, filed Sep. 12, 1997, now U.S. Pat. No. 5,999,848; all of which are assigned to the same assignee as the present application and each of which is incorporated herein by reference in its entirety.

As disclosed in the referenced patents, an improved implantable sensor may be fabricated by placing the electrodes on one side of the substrate and by also placing an integrated circuit (IC) chip on the other side of the substrate, along with other needed electronic components, e.g., a capacitor(s), thereby forming a hybrid electronic circuit on the side of the substrate opposite the electrodes that is used to control or drive the sensor. The sensor senses the electrical current flowing to the electrodes, from which current the amount of oxygen near the electrodes can be determined, from which oxygen level determination, the amount of glucose to which the sensor is exposed can also be determined. Additionally, the sensor sends and receives information, data, and/or power from an external location over a two-conductor transmission line. The IC chip and other electronic components are hermetically sealed under a metal cover, the edges of which are hermetically bonded to the substrate. Electrical connection is established with the IC chip and other sealed components through stair-step vias or passageways that traverse through the substrate. Several of these types of sensors may be daisy-chained together, using just two conductors, as required. The outer sheath encircles the entire substrate, both the electronic circuit side with its metal cover and the sensor electrode side with its electrodes, saline solution reservoir and enzyme-filled window.

Disadvantageously, the sensor described in the referenced patents and patent applications is relatively thick. For many implantable applications, a thinner sensor is needed that still provides hermetic electrical connections to its internal circuitry. Hence, there remains a need for yet a smaller sensor that performs all of the same functions as the prior sensor, i.e., that provides working electrodes exposed to a saline with a selected enzyme placed over one electrode and with hermetically-sealed electronic circuitry controlling the sensor and communicating with other sensors and an external control unit. The present invention advantageously addresses these and other needs.

SUMMARY OF THE INVENTION

The present invention provides an implantable substrate sensor wherein electronic circuitry associated with the sensor, i.e., the IC chip, is formed within, or on, a suitable substrate, e.g., a CMOS substrate. A protective coating then covers the substrate, effectively forming a hermetically sealed package having the circuitry under the coating. In embodiments of the present invention, the circuitry has one or more electrically conductive pads for communicating and/or providing power to the circuitry. One or more electrical pathways provide hermetic electrical connection to the conductive pads for external connection to the sealed circuitry within the sealed package. Electrodes associated with the sensor may be selectively left uncovered by the protective coating, thereby allowing such electrodes to be exposed to body tissue and fluids when the sensor is implanted in living tissue.

In a first embodiment, the electrical pathway is a via that is made from a biocompatible material, e.g., platinum, that is made hermetic by either increasing its thickness, e.g., to at least 5 microns, or by ion beam deposition. Alternatively, the electrical pathways are formed from metal traces essentially parallel to the surface of the substrate that are connected at their first ends by first vias to conductive pads on the circuitry and with their second ends extending external to the sealed package, thus providing external electrical connection to the hermetically sealed circuitry. The metal traces are surrounded by a biocompatible insulation material, e.g., alumina, zirconia, or alloys of alumina and zirconia. Due to this combination of vias and metal traces surrounded by insulation material, the resulting electrical connection is hermetic.

In accordance with one aspect of the invention, a pair of thin substrate sensors made in accordance with the present invention, each having electronic circuitry formed on one side of the substrate may be placed back-to-back with the interconnecting and/or sensing electrodes facing outward. Such a back-to-back pair of substrate sensors advantageously allows the sensor electrodes to be positioned on the outside surfaces of the sensor pair substrates.

A hermetically sealed package suitable for implantation in living tissue comprises (1) a semiconductor substrate having a plurality of surfaces and having an integrated circuit formed on at least one of said surfaces, the integrated circuit having one or more electrically conductive pads for communicating and/or providing power to the integrated circuit, (2) one or more electrical pathways for providing electrical connection to the one or more electrically conductive pads, the pathways having first ends coupled to the one or more pads and second ends exposed for external electrical connection from the sealed package, and (3) an insulating material for encapsulating the integrated circuit and the semiconductor substrate surfaces except for selected portions of the second ends of the electrical pathways.

The novel features of the invention are set forth with particularity in the appended claims. The invention will be best understood from the following description when read in conjunction with the accompanying drawings.

BRIEF DESCRIPTION OF THE DRAWINGS

The above and other aspects, features and advantages of the present invention will be more apparent from the following more particular description thereof, presented in conjunction with the following drawings.

Corresponding reference characters indicate corresponding components throughout the several views of the drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The following description of is of the best mode presently contemplated for carrying out the invention. This is made merely for the purpose of describing the general principles of the invention. The scope of the invention should be determined with reference to the claims.

At the outset, it is to be noted that implantable sensors are generally used to sense some type of physiological parameter or condition or other event that occurs within, or is sensible from a location within, living tissue of a patient. To that end, such sensors employ one or more electrodes, or similar transducers, that convert a sensed parameter to an electrical or other detectable signal. Ofttimes, a sensor simply senses an electro-potential signal, such as that which typically accompanies depolarization of muscle tissue, or other natural electrical signals associated with the patient's body. In such an instance, all the sensor need employ is some type of electrode that is in contact with the monitored tissue and appropriate electronic circuitry for receiving, amplifying and/or storing any signal that is sensed. Also, it is common to employ the electrode of such sensor as a stimulator as well, through which an electrical current pulse may be applied to tissue in contact with the electrode. Thus, it is common to refer to a sensor electrode, which also may be used as a stimulus electrode, as a sensor/stimulator. Further, the sensor may be used as an electrochemical sensor, or enzyme electrode sensor, e.g., of the type disclosed in the '163 patent or the other referenced patents. For such an electrochemical sensor, a suitable enzyme or other chemical is placed in close proximity to the electrodes so that the desired chemical interactions may take place.

Whatever the type of implantable sensor employed, a common element(s) in all such sensors is the electrode and the electronic circuitry used to monitor and/or control the electrode(s). It is to be understood, however, that other sensor elements, e.g., an enzyme, may be used in conjunction with the electrode and associated electronic circuitry.

To better understand and appreciate the advantages offered by the present invention, it will first be helpful to briefly review a preferred application and manner of making an implantable sensor of the type disclosed in the referenced patent and patent applications. To that end, reference is made to FIG. 1, where there is shown a block diagram that illustrates multiple sensor/stimulators 12a, 12b, . . . 12n, connected together, as well as to a controller (not shown) using just two common conductors 14 and 16. The two conductors 14 and 16 provide a common signal and return for data signals and power signals that are sent from the controller to the sensor/stimulators 12a, 12b. . . . 12n, as well as a common signal and return path for data signals transmitted from the sensor/stimulators 12a, 12b, . . . 12n, to the controller.

Figure 2:
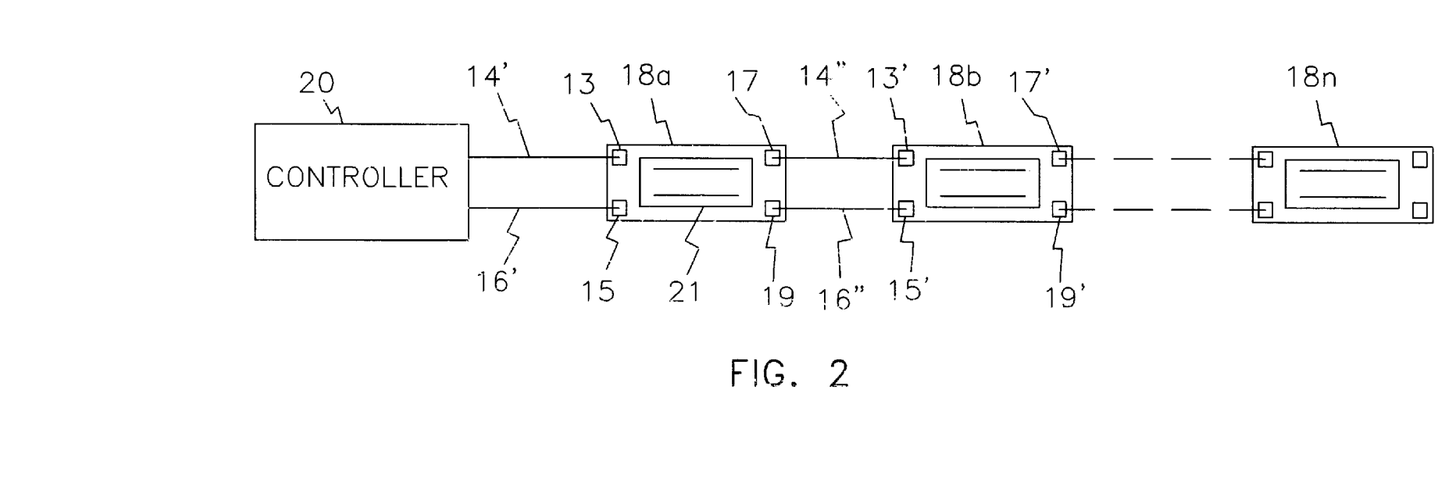
FIG. 2 schematically illustrates a preferred manner of how a sensor/stimulator may be connected with a controller and other sensors/stimulators in a serial or daisy-chain fashion.

FIG. 2 schematically illustrates how an implantable device, e.g., a sensor/stimulator 18a, may be connected with a remote controller 20 and other implantable sensor/stimulators 18b, . . . 18n, in a serial or daisy-chain fashion. As seen in FIG. 2, the sensor/stimulator 18a is connected to the controller 20 by two conductors 14' and 16' which are attached to a first pair of pads or terminals 13 and 15 along a proximal side (i.e., the side closest to the controller 20) of the sensor/stimulator 18 a. Another pair of pads or terminals 17 and 19 are located along a distal side (i.e., the side farthest from the controller 20) of the sensor/stimulator 18a.

As will become evident from the description that follows, the distal pad 17 is electrically connected to the proximal pad 13 through the circuitry 21 located on the sensor/stimulator 18a. Similarly, the distal pad 19 is electrically connected to the proximal pad 15 through the circuitry 21 included within the sensor/stimulator 18a. Two additional conductors 14" and 16" are then used to connect the distal pads 17 and 19 of the device 18a to corresponding proximal pads 13' and 15' of the next sensor/stimulator 18b connected in the daisy chain. In this manner, as many devices as desired may be serially connected to the controller 20 using just two conductors.

Figure 1:
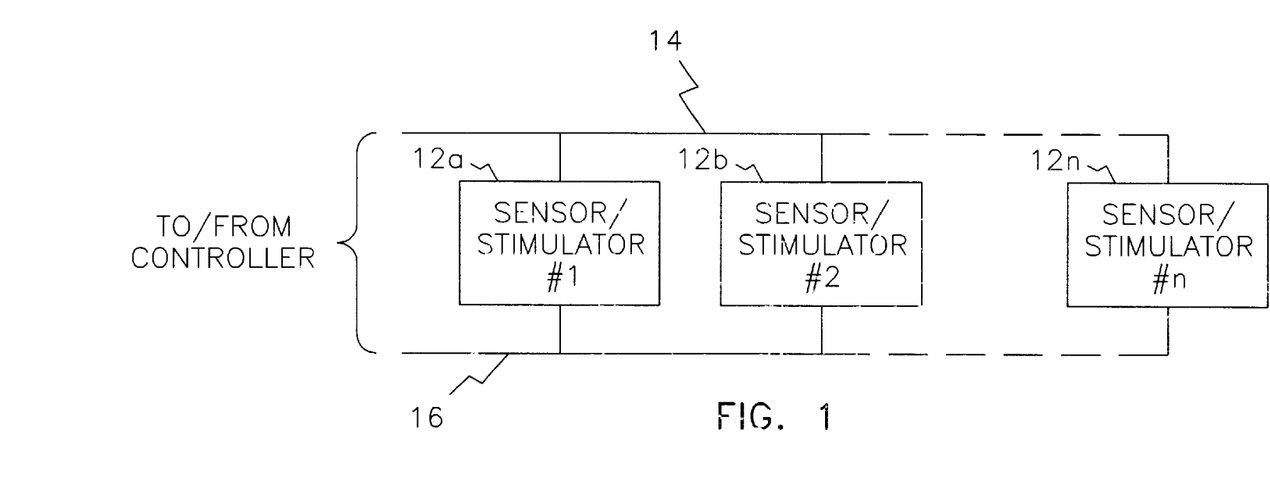
FIG. 1 is a block diagram that illustrates multiple sensors/stimulators connected together using a two-conductor bus, which two-conductor bus may be connected to a controller.

It is noted that FIG. 1 is functionally electrically equivalent to FIG. 2. FIG. 2 simply employs proximal and distal pairs of pads or terminals to facilitate the connection of additional devices to the chain by extending two conductors from the distal pads 17 and 19 of a more proximal device in the chain to the proximal pads 13' and 15' of a new device to be added to the chain. However, where the particular application allows connections to be made to, or branched off of, the two main conductors 14 and 16, then the configuration of FIG. 1 may be used just as well as the configuration of FIG. 2.

There exist many different applications for the daisy-chainable sensor/stimulators 12 or 18 of the system illustrated in FIGS. 1 or 2. Generally, where the sensor/stimulators 12 or 18 are implanted, they are designed to sense one or more body parameters or substances found in body tissue or fluids, e.g., glucose level, blood pH, $O_2$, temperature, or the like. Such measurements can provide valuable information regarding the condition and status of the patient. As such, it is ofttimes desirable to make more than one measurement within the same general body tissue area so as to be able to compute an average or mean of the measurements thus made or otherwise obtain a consensus from several different readings, thereby better assuring the accuracy and reliability of the data thus gathered.

Other times, it may be desirable to obtain various measurements of a given substance at physically related, but different, body locations. For example, for some applications, e.g., a closed-loop insulin infusion system, it could be advantageous to obtain a glucose reading within the blood stream and another glucose reading within the blood stream and another glucose reading within the body tissue adjacent the blood stream. This is because the time constant associated with how readily one glucose reading changes compared with the other may be different (and, in fact, is usually different), and being able to obtain or monitor such difference would provide valuable information regarding the regulation of the insulin infusion.

Turning next to FIGS. 3A, 3B, 3C and 3D, there are shown, respectively, a perspective exploded view (FIG. 3A), a side view (FIG. 3B), a top view (FIG. 3C), and an end view (FIG. 3D), of a typical implantable sensor device 30 of the type disclosed in the referenced patents. As seen best in FIG. 3A, the sensor device 30 typically includes a carrier or substrate 36 on which an integrated circuit (IC) 38 and other components, such as a capacitor 40, are mounted in hybrid fashion.

Figure 3A:
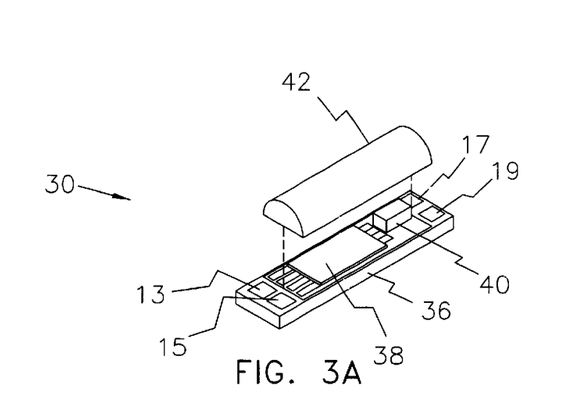
FIG. 3A shows a perspective, partially exploded, view of a sensor/stimulator of the type disclosed in the referenced patent application as used in the daisy chain of FIG. 2.

Whereas the carrier or substrate 36 shown in FIG. 3A serves as a foundation or base on which hybrid electronic circuitry is formed, the present invention relates to an embodiment where the carrier or substrate 36 actually comprises the substrate in which the IC 38 is formed.

For the embodiment shown in FIGS. 3A–3D, all of the components of the hybrid circuit are hermetically sealed within a cavity formed by a lid or cover 42 which is bonded to the substrate 36. As will be evident from the description that follows, a significant advantage of the present invention is that this lid or cover 42 is not required in the embodiment of the invention disclosed herein.

Returning to FIGS. 3A–3D, proximal pads or terminals 13 and 15, as well as distal pads or terminals 17 and 19, remain outside of the hermetically sealed part of the hybrid circuit created by the cover 42. These proximal and distal pads, however, are electrically connected to the circuitry within the hermetically sealed part through suitable feedthrough connections. One preferred manner of making such feedthrough connection is to use a feedthrough connection that passes through the carrier or substrate in the stair-step manner (including both vertical and horizontal segments) is disclosed in U.S. Pat. No. 5,750,926, which '926 patent is incorporated herein by reference.

Still with reference to FIGS. 3A–3D, on the side of the carrier or substrate opposite the hybrid electrical circuitry, a suitable electrochemical sensor 44, or other desired type of sensor or stimulator, may be formed or located. A type of electrochemical sensor that may be used, for example, is the enzyme electrode sensor described in U.S. Pat. No. 5,497,772, incorporated herein by reference, and in particular, in FIGS. 2A, 2B, 2C, 3, 4A and 4B of that patent. However, it is to be emphasized that the precise nature of the sensor 44, or other implantable element used within the sensor device 30, is not critical to the present invention. All that matters is that the sensor or other element be implantable, and that it provide a desired function, e.g., sense a certain type of parameter or substance, or generate a certain type of signal, in response to an appropriate control signal or signals.

Figures 3B, 3D, 4:
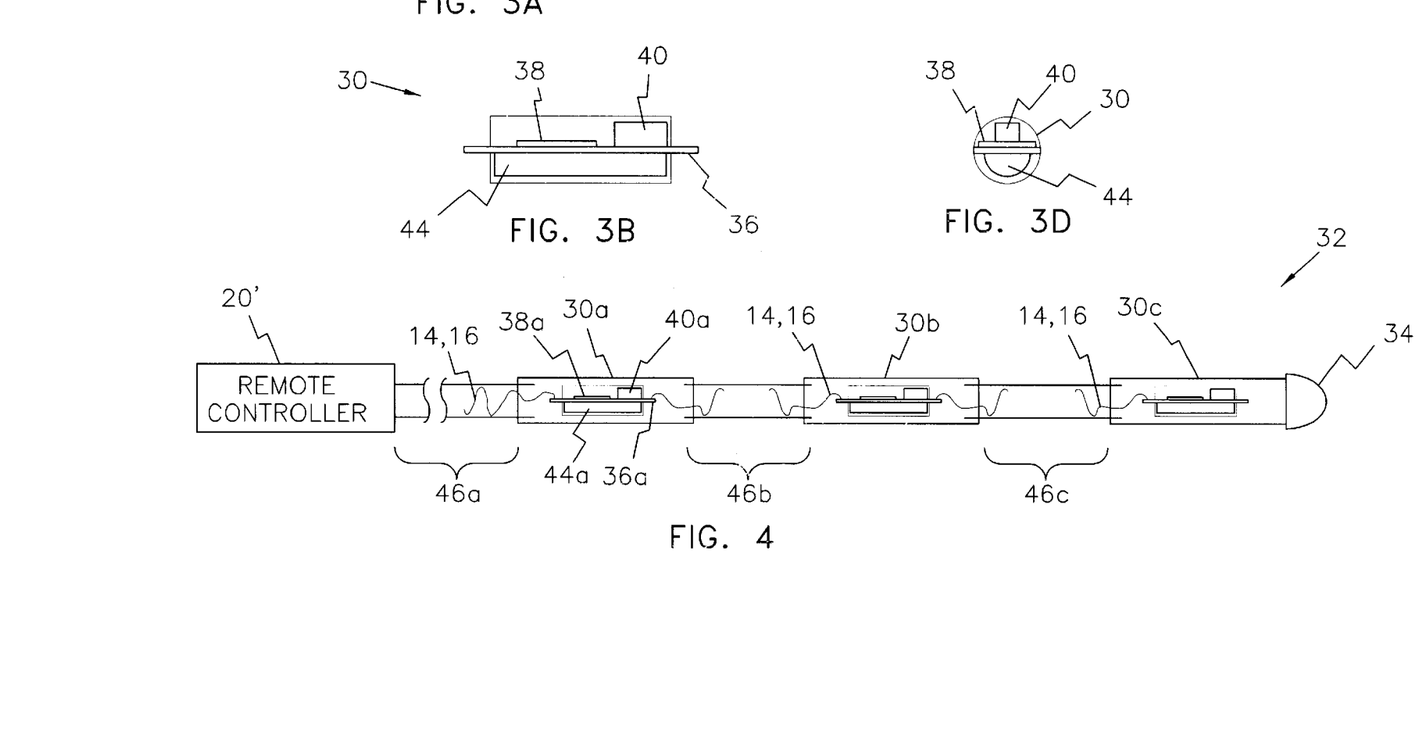
FIG. 3B illustrates a sectional side view of the sensor/stimulator of FIG. 3A.
FIG. 3D illustrates a sectional end view of the sensor/stimulator of FIG. 3A.
FIG. 4 depicts an implantable lead that includes a plurality of the sensor/stimulators of FIGS. 3A–3D.
Figure 3C:
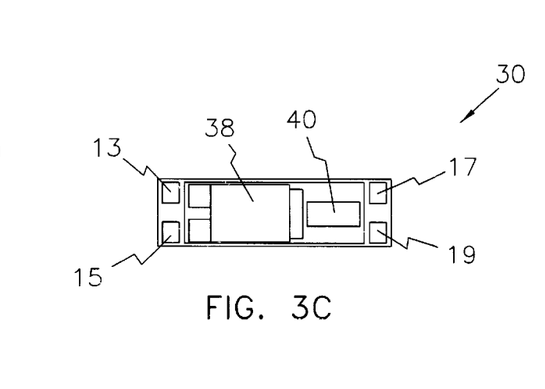
FIG. 3C illustrates a sectional top view of the sensor/stimulator of FIG. 3A.

Whatever type of control signal(s) or output signal(s) is/are generated by the sensor 44, or other element, such signal(s) may be communicated from the hybrid circuit side of the carrier or substrate 36 (which is the top side as the sensor device 30 as oriented in FIG. 3B or FIG. 3D, and which top side includes the hermetically sealed portion of the device) to the sensor side of the sensor device 30 (which is the bottom side as shown in FIG. 3B or FIG. 3D) by way of appropriate hermetically-sealed feedthroughs that pass step-wise from the hybrid (top) side of the sensor device 30 through the substrate or carrier, e.g., in the manner set forth in the above-referenced '926 patent, to the sensor (bottom) side of the sensor device 30.

For example, where the sensor comprises a glucose sensor of the type taught in U.S. Pat. No. 5,497,772, there may be five conductors that electrically interface with the main elements (electrodes) of the sensor, as seen best in FIG. 4A of the '772 patent. Where such a glucose sensor is employed, these five conductors thus interface with the hybrid electrical circuitry found on the top side of the carrier 36 using appropriate feedthroughs that hermetically pass step-wise through the carrier 36, i.e., that pass through the carrier using both vertical horizontal segments, as taught in the '926 patent.

As mentioned above, the parent application is directed to a device 30 that does not employ a carrier 36, per se, as shown in FIGS. 3A, 3B, 3C, 3D and FIG. 4, wherein the control electronics are positioned on one side (the top side) of the carrier 36, and the sensor, or other device being used with or controlled by the electronics, is placed on the other side (the bottom side) of the carrier. Rather, the ceramic or substrate on which the IC 38 is formed itself functions as the carrier. In the parent application, this is accomplished using vias that are formed in a substrate, or between various layers of an integrated circuit as the integrated circuit (IC) is formed, function as hermetic feedthroughs, with selected layers and traces being coated as needed with aluminum oxide, or other oxide coatings, in the manner taught in the aforementioned '926 patent, and/or in U.S. patent application Ser. No. 08/994,515, filed Dec. 19, 1997, now U.S. Pat. No. 6,043,437, incorporated herein by reference, in order to seal appropriate sections or portions of the IC so that the coated IC may itself be implanted. Advantageously, when this is done, the sensor 44 or other implantable element used with or controlled by the IC may be formed on the back side (non-active side) of the IC substrate. Thus, a carrier, per se, is not needed because the IC substrate functions as the carrier, and a lid or cover 42 is not needed.

An important advantage achieved with embodiments of the parent application is that the electrical circuitry formed within the substrate of the sensor allows the implantable device to be daisy chained with other similar implantable devices, while still allowing each individual device to be individually addressed, controlled and monitored from a single controller 20. Such electrical circuitry, frequently referred to hereafter as the interface/control circuitry, is shown in FIGS. 3A, 3B, 3C, 3D and 4 as being located on the "top" side of the carrier 36, predominantly underneath the cover 42 in a hermetically sealed portion of the sensor device 30. However, it is to be understood that in accordance with the parent application, such interface/control is actually formed within the substrate, on an active side of such substrate, and coated, as required, with a suitable coating, so as to be hermetically sealed.

The configuration of FIG. 2 is especially well-suited where several of the implantable devices are to be daisy-chained together to form a single lead 32, as shown in FIG. 4. As seen in FIG. 4, three sensor-type devices 30a, 30b, and 30c of the type shown in FIGS. 3A–3D are connected together via lead segments 46a, 46b, and 46c. Each of the lead segments 46a, 46b, and 46c, contain two conductors 14, 16, and may be constructed in any suitable manner, e.g., with the two conductors being spirally wound within the lead segments, and with the spiral windings being encased or covered within a sheath of silicone rubber, as in known in the lead art. (Note, that for purposes of FIG. 4 each of the two conductors 14,16 within the lead 32 is considered as one conductor, even though each is segmented within the individual lead segments 46a, 46b and 46c as it connects from the distal pad of one device to the proximal pad of another device.) A distal cap 34 covers the distal pads of the end, or most-distal, sensor device 30c of the lead 32.

Figure 5A:
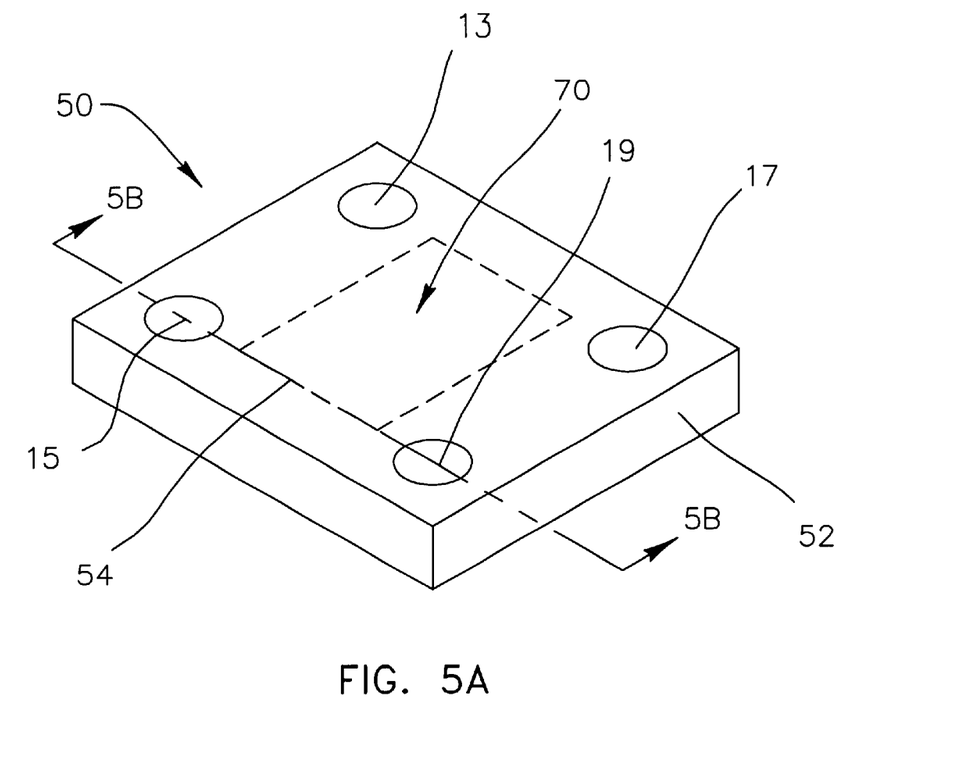
FIGS. 5A and 5B respectively shows perspective and cross sectional views of a preferred sensor substrate made in accordance with the present invention, which provides a hermetic electrical connection to a semiconductor formed on the substrate by enhancing the hermeticity of the electrically conductive via.
Figure 5B:
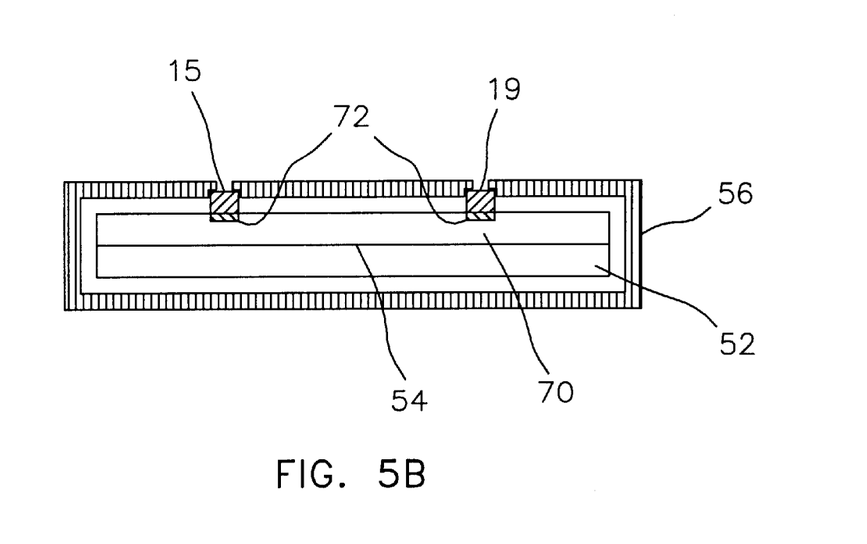

Turning next to FIGS. 5A and 5B, a preferred substrate sensor 50 made in accordance with the present invention is shown. Top and sectional side views of such substrate sensor 50 are shown in FIGS. 5A and 5B, respectively. Advantageously, the substrate sensor 50 does not use hybrid electronic circuitry nor require a hermetically-sealed lid or cover. Rather, the substrate sensor 50 includes a substrate 52, e.g., a silicone or ceramic substrate of the type commonly used in the formation of CMOS or other integrated circuits.

Electronic circuitry is formed as an integrated circuit 70 on an active side of the substrate 52, within a region 54, in conventional manner, e.g., in accordance with conventional CMOS processing techniques, and may extend down below the surface into the substrate 52. Hence, the circuit region 54 is shown in FIG. 5B as extending slightly into the body of the substrate 52. On the active surface of the substrate sensor 50, as seen in FIG. 5A, connection pads 13, 15, 17 an 19 may be formed to allow the sensor substrate to be daisy-chained with other sensors, as taught in the previously referenced U.S. Pat. No. 5,999,848.

The integrated circuit 70 (shown in the example of FIG. 5B as extending to the edge of the substrate 52) includes a plurality of electrically conductive pads 72 formed on its upper surface for communicating and/or providing power to the integrated circuit 70. Such pads are formed from an electrically conductive material, e.g., aluminum, or the like, in a conventional matter. The majority of the substrate 52 and the integrated circuit 70 formed within are coated with a biocompatible insulating material, e g., alumina, zirconia, or an alloy or alumina and zirconia, to hermetically encapsulate the package forming the substrate sensor 50 using an encapsulation layer 56. Significantly, the present invention provides electrical connection through the encapsulation layer 56 to the electrically conductive pads 72 while maintaining the hermeticity of the package forming the substrate sensor 50. In a first embodiment, shown in FIG. 5B, a metallic via (e.g., forming pads 15 and 19), preferably formed from platinum, passes through the encapsulation layer 56 in order to provide external electrical connection to the electrically conductive pads 72. The vias are preferably made hermetic in one of two techniques. In a first technique, the layer of platinum forming the via is made thick enough, e.g., at least 5 microns, to overcome any non-uniformity of the platinum that would tend to allow leakage. In a next technique, described further below, ion beam deposition can be used to form the platinum vias. Since, this process will form a more uniform layer of platinum, the thickness of the platinum vias may be somewhat decreased while still being hermetic.

Figure 6A:
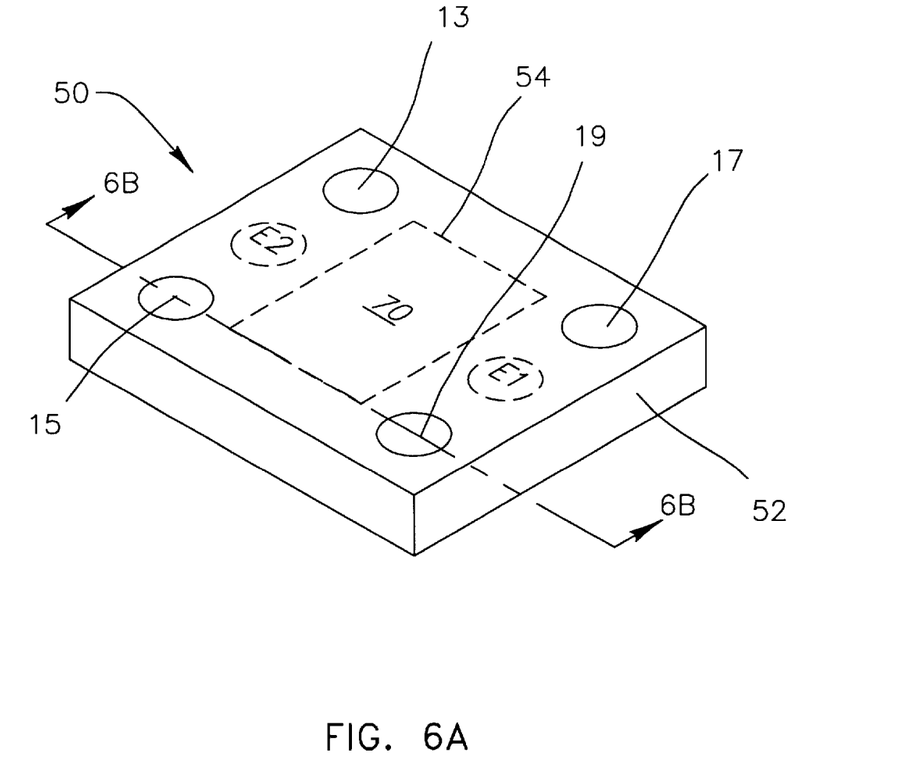
FIGS. 6A and 6B respectively shows a perspective and a cross sectional view of an alternative embodiment of a preferred sensor substrate made in accordance with the present invention, which provides a hermetic connection to a semiconductor formed on substrate by forming a combination of via and metallic pathways surrounded by an insulating material.
Figure 6B:
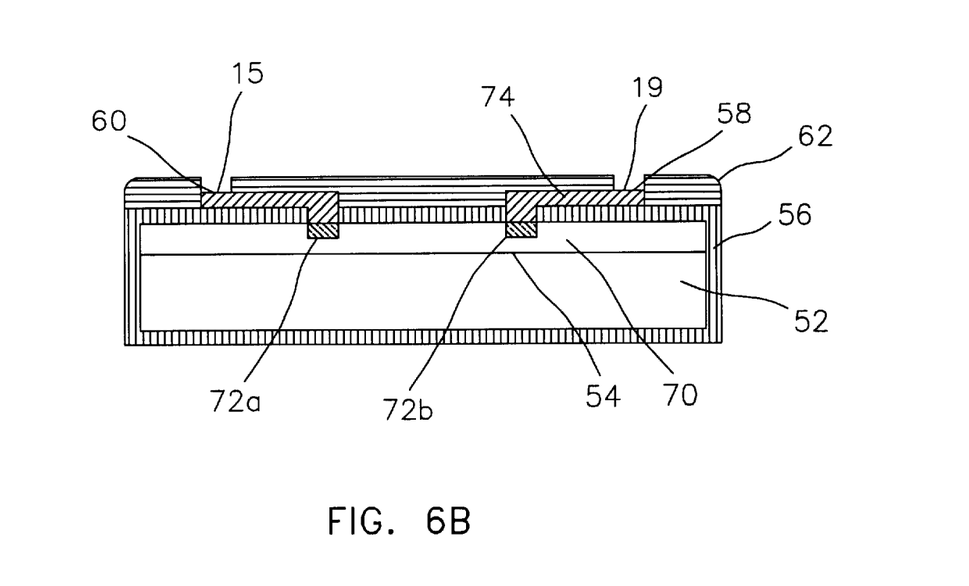

Turning next to FIGS. 6A and 6B, an alternative technique is shown for providing external hermetic electrical connections through the encapsulation layer 56 to the electrically conductive pads, e.g., 72a and 72b, on the integrated circuit 70 (shown in the example of FIG. 6B as extending to the edge of the substrate 52). In this technique, a metallic (e.g., aluminum, platinum) trace, e.g., trace 74, is formed essentially parallel to the surface of the substrate 52 and the integrated circuit 70. A first end of the trace 74 is electrically coupled to the electrically conductive pad, e.g., pad 72b. A second end 58 of the trace 74 is exposed through the encapsulation material 56 to form a pad 19 accessible at its outer surface. In the technique shown in FIG. 6B, hermeticity is achieved via the serpentine routing of the electrical connection from the second end 58 of trace 74 to the conductive pad 72b and by the relative length of the metal trace 74, e.g., the length of the metal trace is preferably at least 100 microns. Preferably, the metal trace is surrounded by thin, e.g., 1 micron, layers of encapsulation material, typically deposited as one or more fabrication steps.

Additional electrical connections, e.g., for forming sensing electrodes E1 and E2 (see FIG. 6A), may also be formed on the same surface as the power/communication pads 13, 15, 17, 19 and hermetically connected to the integrated circuit 70 in a similar manner. Such sensing electrodes may be used in combination with the integrated circuit 70 to form a sensor as described in the aforementioned patents. Advantageously, when desired, the previously described technique allows all of the connections, circuitry and sensing electrodes to be formed on the same surface of the substrate 52 and thus facilitates the fabrication of multiple, e.g., pairs of, sensors as described further below in the description of FIGS. 9 and 10.

Figure 7:
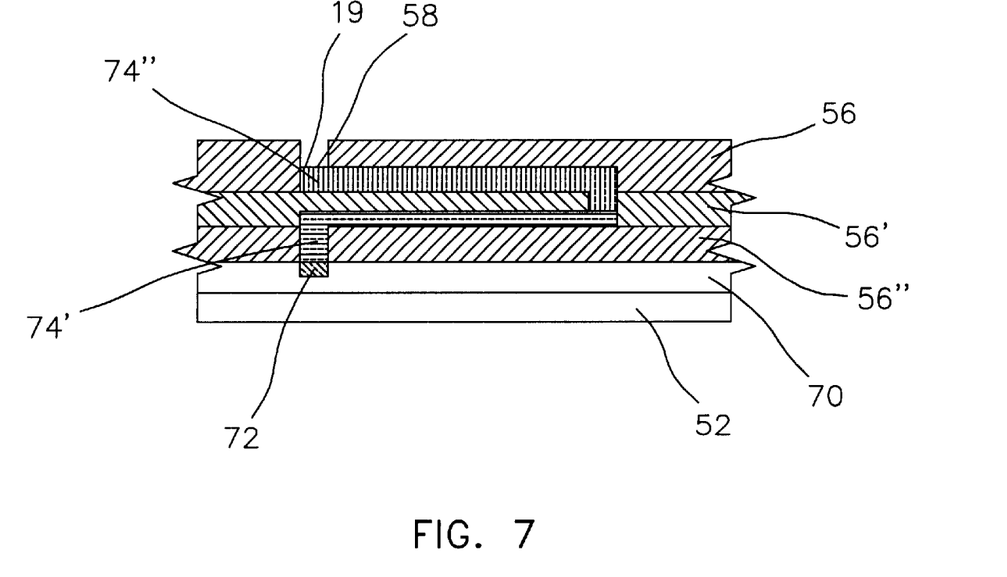
FIG. 7 shows a partial cross section of a next alternative embodiment of a technique for providing a hermetic electrical connection to the semiconductor formed on the substrate.

FIG. 7 shows a partial cross section of a next alternative embodiment of a technique for providing a hermetic electrical connection to the semiconductor formed on the substrate. This embodiment is similar to that shown in reference to FIG. 6A except that additional layers of interconnected metallic electrically conductive traces, 74', 74" surrounded by additional encapsulation layers 56', 56", 56''' are used to further enhanced the hermeticity of the electrical connection (at some cost in increased thickness of the package).

Various techniques may be used to apply a coating of encapsulation layer 56, e.g., alumina insulation, over the substrate 52. A preferred technique, for example, is to use an ion beam deposition (IBD) technique. IBD techniques are known in the art, as taught, e.g. in U.S. Pat. Nos. 4,474,827 or 5,508,368, incorporated herein by reference.

Figure 8:
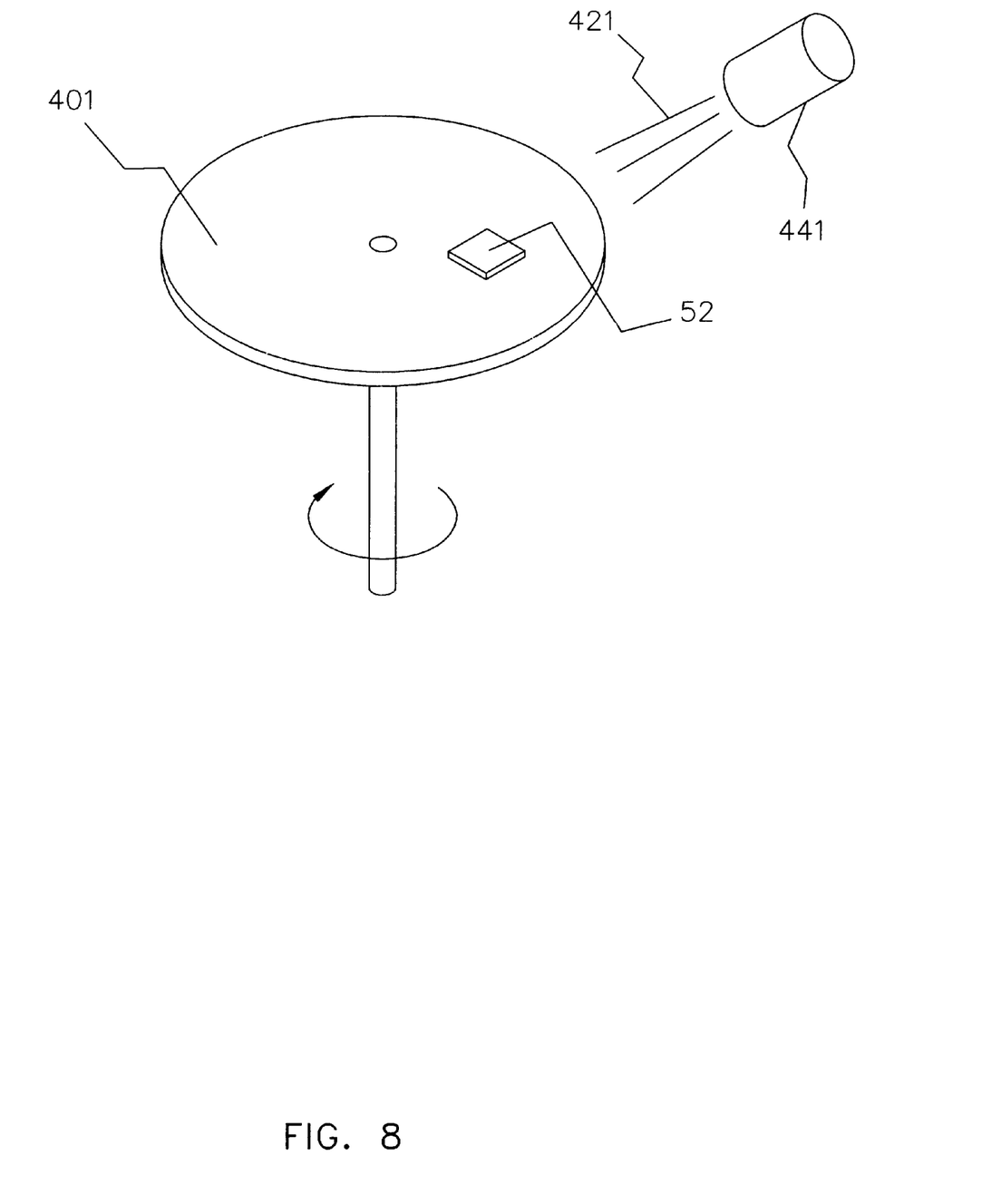
FIG. 8 shows one method that may be used to deposit a protective coating or layer over the sensor substrate.

Using such IBD techniques, or similar techniques, the desired alumina or other layer 56 may be deposited on all sides of the substrate 52 as illustrated in FIG. 8. As seen in FIG. 8, the substrate 52 is placed on a suitable working surface 401 that is rotatable at a controlled speed. The working surface 401 with the substrate 52 thereon (once the circuitry and electrodes have been formed thereon) is rotated while a beam 421 of ions exposes the rotating surface. Assuming the substrate 52 has six sides, five of the six sides are exposed to the beam 421 as it rotates, thereby facilitating application of the desired layer of alumina onto the five exposed sides of the object. After sufficient exposure, the object is turned over, thereby exposing the previously unexposed side of the substrate to the beam, and the process is repeated. In this manner, four of the sides of the substrate 52 may be double exposed but such double exposure simply results in a thicker encapsulation layer 56 of alumina on the double-exposed sides.

Other techniques, as are known in the art, may also be used to apply the alumina encapsulation layer 56 to the object.

The steps typically followed in applying an encapsulation layer 56 of alumina to the substrate 52 include:

(a) Sputtering a layer of titanium of about 300 Å thick over any metal conductor or other object that is to be coated with the alumina.

(b) If selective application of the alumina to the object is to be made, spinning a photosensitive polyamide onto the substrate.

(c) Applying a mask that exposes those areas where alumina is not to be applied.

(d) Shining ultraviolet (UV) light through the mask to polymerize the polyamide. Where the UV light illuminates the polyamide is where aluminum oxide will not be deposited. Thus, the polymerizations of the polyamide is, in effect, a negatively acting resist.

(e) Developing the photoresist by washing off the unpolymerized polyamide with xylene, or an equivalent substance. Once the unpolymerized polyamide has been washed off, the ceramic (or other component) is ready for aluminum oxide deposition.

(f) If selective application of the alumina is not to be made, i.e., if alumina is to be applied everywhere, or after washing off the unpolymerized polyamide, depositing aluminum oxide to a prescribed thickness, e.g., between 4 and 10 microns, e.g., 6 microns, over the subject using ion enhanced evaporation (or sputtering), IBD, or other suitable application techniques.

(g) During application of the coating, rotate and/or reposition the substrate as required in order to coat all sides of the substrate, e.g., as shown in FIG. 8, with a coating of sufficient thickness. This step may require several iterations, e.g., incrementally depositing a thin layer of alumina, checking the layer for the desired thickness or properties, and repeating the repositioning, depositing, and checking steps as required until a desired thickness is achieved, or until the coating exhibits desired insulative and/or hermeticity properties.

(h) Breaking or scribing the aluminum oxide that resides over the polyamide, if present, with a diamond scribe, or laser, controller by a computerized milling machine. This permits a pyrana solution, explained below, to get under the oxide for subsequent lift off of the aluminum oxide.

(i) Lifting off the polyamide and unwanted aluminum oxide after soaking the substrate in pyrana solution ($H_2SO_4 \times H_2O_2 \times 2$ heated to 60° C.). Soaking should occur for 30 to 60 minutes, depending on the thickness of the polyamide layer.

The above described coating method is substantially the same as that disclosed in the referenced U.S. Pat. No. 6,043,437, previously incorporated herein by reference. It should be apparent to one of ordinary skill in the art that the aforementioned IBD techniques may be adapted to selectively deposit a layer of platinum or the like of a biocompatible electrically conductive metal to form the via and electrodes used to provide an external electrical interconnection to the semiconductor formed within. Advantageously, by using such an IBD technique, the platinum or the like metallic layer can be made sufficiently uniform to provide a hermetic connection.

Figure 9:
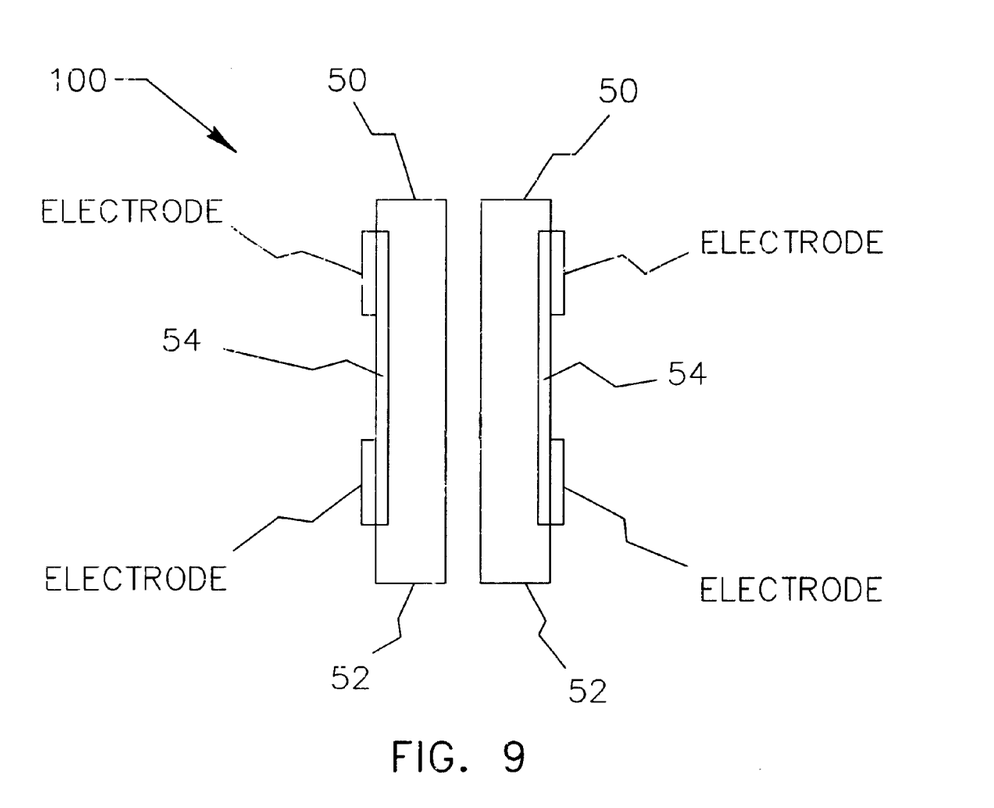
FIG. 9 illustrates a sensor assembly formed by placing two sensor substrates back-to-back so that the electrodes of both sensor substrates face outwardly from the assembly.

FIG. 9 illustrates a sensor assembly 100 formed by placing two sensor substrates 50 back-to-back so that the electrodes of both sensor substrates face outward. The protective encapsulation layer 56 is not shown in FIG. 9, but it is presumed to be present.

Figure 10:
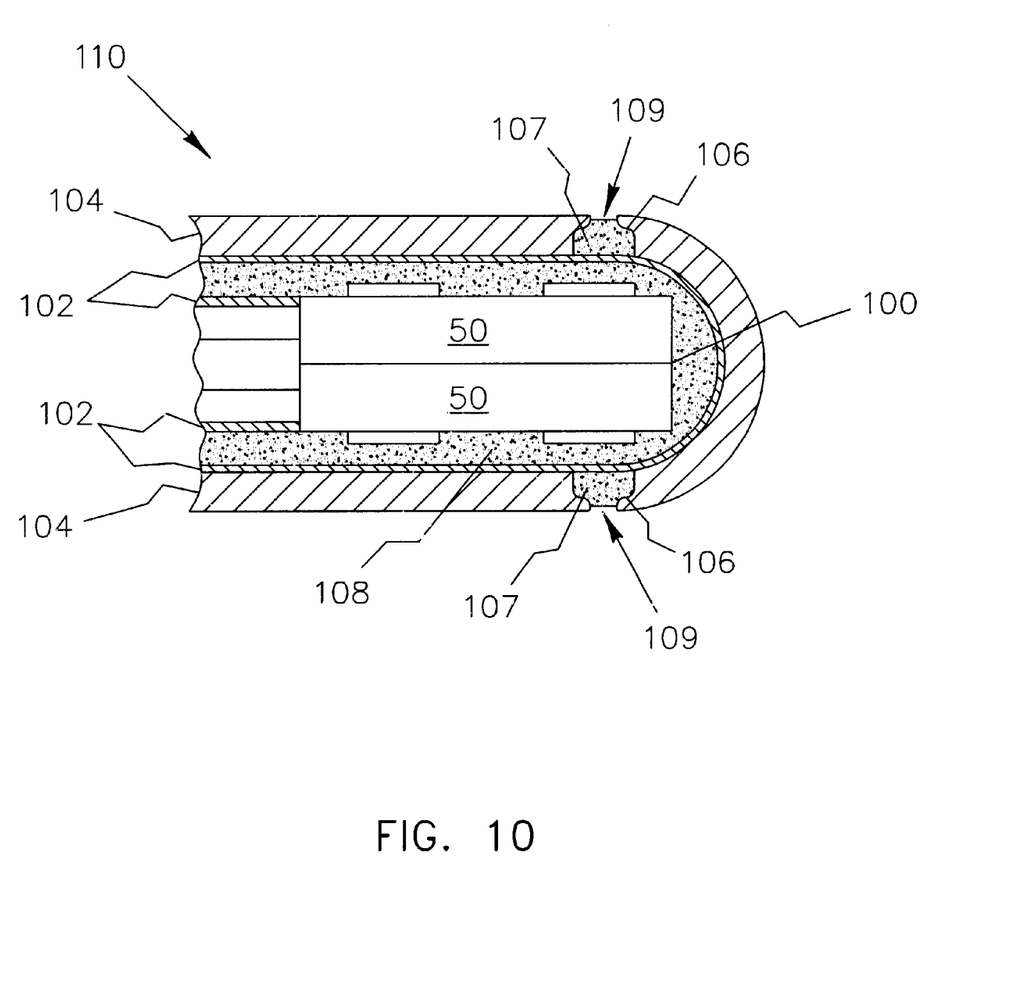
FIG. 10 depicts use of the sensor assembly of FIG. 9 within a sheath and membrane to form an electrochemical sensor assembly.

FIG. 10 depicts the use of the sensor assembly 100 of FIG. 9 within a sheath 102 and membrane 104 so as to form an electrochemical sensor assembly 110. The sheath 102 surrounds the sensor assembly 100 and forms a reservoir therein into which a suitable solution 108, e.g., a saline solution, is held. The membrane 104 surrounds the sheath 102. Pockets 106 are formed in the membrane 104 over a selected working electrode. A suitable enzyme 107 is placed inside of the pockets. Windows 109 expose the enzyme 107 to the surrounding environment held in the pockets 106.

Operation of the electrochemical sensor assembly 110 may be substantially as described in the '163 patent and the other previously referenced patents. However, in the aforedescribed structure of sensor assembly 110, the sensing windows 109 are located on both sides of the assembly, thereby providing a broader exposure coverage or "view" for the operation of the sensor.

As described above, it is thus seen that the present invention provides and implantable sensor having electrodes and electronic circuitry, where the electronic circuitry and electrodes are formed on or in the same substrate material, e.g., a semiconductor substrate of the same type used in the formation of complementary metal oxide semiconductor (CMOS) integrated circuits.

It is a further seen that the invention provides and implantable sensor, including electrodes and electronic circuitry, that does not require a lid or cover for hermetically sealing hybrid electronic circuitry on one side of a substrate; thereby allowing the sensor to be significantly thinner than would otherwise be possible.

While the invention herein disclosed has been described by means of specific embodiments and applications thereof, numerous modifications and variations could be made thereto by those skilled in the art without departing from the scope of the invention set forth in the claims. For example, it is generally desirable that the corners of the assembly be rounded (see corner 62 in FIG. 6B) to further ensure hermeticity. Sandblasting and acid etching techniques can accomplish this rounding. Furthermore, while pads, e.g., 19, are generally positioned within a shallow cavity in the encapsulation layer 56, it may be desired to bond conductive beads or pads to assist external connection or to stagger/layer the surrounding encapsulation layer to minimize any stress on external connections to the pads, e.g., 19. Such variations are considered to be within the scope of the present invention. It is therefore to be understood that within the scope of the claims, the invention may be practiced otherwise than as specifically described herein.

What is claimed is:

1. A hermetically sealed package suitable for implantation in living tissue, said package comprising:
    a semiconductor substrate having a plurality of surfaces and having an integrated circuit formed as an integral portion of at least one of said surfaces, said integrated circuit having one or more electrically conductive pads for communicating and/or providing power to said integrated circuit;
    one or more electrical pathways formed as an integral portion of said semiconductor substrate for providing electrical connection to said one or more electrically conductive pads, said pathways having first ends coupled to said one or more pads and second ends exposed for external electrical connection from said sealed package, wherein said second ends are formed from biocompatible material having sufficient uniformity and/or thickness to ensure hermeticity of said electrical pathways; and
    an insulating coating material for encapsulating said integrated circuit and said semiconductor substrate surfaces except for selected portions of said second ends of said electrical pathways wherein said hermetically sealed package is thereby suitable for implantation in living tissue without further packaging.

2. The hermetically sealed package of claim 1 wherein said electrical pathways are comprised of platinum.

3. The hermetically sealed package of claim 2 wherein said platinum electrical pathways are made hermetic by using ion beam deposition to ensure sufficient uniformity.

4. The hermetically sealed package of claim 2 wherein said platinum electrical pathways are made hermetic by having the thickness of the platinum via being at least 5 microns.

5. The hermetically sealed package of claim 1 wherein said integrated circuit is formed on a first surface of the semiconductor substrate and said electrical pathways from said integrated circuit extend outward from said first surface.

6. The hermetically sealed package of claim 5 wherein said semiconductor substrate has a second surface on a side opposite of said first surface of said substrate and said second surface of said substrate and is formed without electrical pathways or an integrated circuit, thereby facilitating connection of said second surface to a second substrate surface of an additional one of said packages.

7. A hermetically sealed package suitable for implantation in living tissue, said package comprising:
    a semiconductor substrate having a plurality of surfaces and having an integrated circuit formed on at least one of said surfaces, said integrated circuit having one or more electrically conductive pads for communicating and/or providing power to said integrated circuit;
    one or more electrical pathways for providing electrical connection to said one or more electrically conductive pads, said pathways having first ends coupled to said one or more pads and second ends exposed for external electrical connection from said sealed package;
    an insulating material for encapsulating said integrated circuit and said semiconductor substrate surfaces except for selected portions of said second ends of said electrical pathways; and wherein each of said electrical pathways comprises:
        a first electrically conductive via electrically coupled to one of said pads;
        a metal trace having first and second ends oriented essentially parallel to the surface of the semiconductor substrate and electrically coupled at said first end to said first via, wherein said second end is at least partially externally exposed; and wherein
        said electrical pathway is surrounded by a biocompatible insulation material.

8. The hermetically sealed package of claim 7 wherein said biocompatible insulation material is selected from the group of alumina, zirconia, or an alloy of alumina and zirconia.

9. The hermetically sealed package of claim 7 wherein said second end of said metal trace is biocompatible.

10. The hermetically sealed package of claim 9 wherein said second end of said metal trace is platinum.

11. A hermetically sealed package suitable for implantation in living tissue, said package comprising:
    a semiconductor substrate having a plurality of surfaces and having an integrated circuit formed on at least one of said surfaces, said integrated circuit having one or more electrically conductive pads for communicating and/or providing power to said integrated circuit;
    one or more electrical pathways for providing electrical connection to said one or more electrically conductive pads, said pathways having first ends coupled to said one or more pads and second ends exposed for external electrical connection from said sealed package;
    an insulating material for encapsulating said integrated circuit and said semiconductor substrate surfaces except for selected portions of said second ends of said electrical pathways; and wherein at least one of said electrically conductive pathways is comprised of:
        a plurality of metal traces having first and second ends, including at least an innermost trace closest to said semiconductor substrate and an outermost trace furthest from said semiconductor substrate, each adjacent pair of metal traces separated by an insulating material sandwiched in-between so as to form a hermetic seal between said metal traces;
        at least one interconnection via surrounded by said insulating material for interconnecting said adjacent pairs of metal traces;
        at least one innermost via for interconnecting said innermost trace to at least one of said pads on said integrated circuit;
        an insulating material for encapsulating said plurality of metal traces, said integrated circuit and said semiconductor substrate, wherein the second end of at least one outermost metal trace is at least partially exposed through the encapsulating insulating material for external communication; and wherein
        said combination of metal traces, sandwiched insulating material, encapsulating material and vias provides a hermetic communication path to said integrated circuit from a location external to said implantable package.

12. A method of forming an electrically conductive hermetic connection to a hermetically sealed integrated circuit, said method comprising the steps of:

forming an integrated circuit as an integral portion of the face of a semiconductor substrate, said integrated circuit having one or more electrically conductive pads for communicating and/or providing power to said integrated circuit;

forming one or more electrical pathways as an integral portion of said semiconductor substrate for providing electrical connection to said one or more electrically conductive pads; said pathways having first ends coupled to said one or more pads and second ends exposed for external electrical connection from said sealed integrated circuit, wherein said second ends are formed from biocompatible material having sufficient uniformity and/or thickness to ensure hermeticity of said electrical pathways; and encapsulating said semiconductor substrate and said integrated circuit except for selected portions of said second ends of said electrical pathways with an insulating coating material wherein said hermetically sealed circuit is thereby suitable for implantation in living tissue without further packaging.

13. The method of claim 12 wherein the step of forming one or more electrical pathways comprises the step of forming said electrical pathways from platinum such that said electrical pathways are biocompatible.

14. The method of claim 13 wherein the step of forming said electrical pathways from platinum comprises depositing said platinum using ion beam deposition to ensure sufficient uniformity.

15. The method of claim 13 wherein the step of forming said electrical pathways from platinum comprises depositing a layer of platinum of at least 5 microns to cause said platinum electrical pathways to be hermetic.

16. The method of claim 12 additionally comprising the step of rounding at least one corner of said encapsulated integrated circuit.

17. The method of claim 16 wherein said rounding step comprises sandblasting.

18. The method of claim 16 wherein said rounding step comprises acid etching.

19. A method of forming an electrically conductive hermetic connection to a hermetically sealed integrated circuit, said method comprising the steps of:

forming an integrated circuit on a face of a semiconductor substrate, said integrated circuit having one or more electrically conductive pads for communicating and/or providing power to said integrated circuit;

forming one or more electrical pathways for providing electrical connection to said one or more electrically conductive pads; said pathways having first ends coupled to said one or more pads and second ends exposed for external electrical connection from said sealed integrated circuit;

encapsulating said semiconductor substrate and said integrated circuit except for selected portions of said second ends of said electrical pathways; and wherein the step of forming one or more electrical pathways comprises at least in part the steps of:

forming a first electrically conductive via electrically coupled to one of said pads;

forming a metal trace having first and second ends oriented essentially parallel to the surface of the semiconductor substrate and electrically coupled at said first end to said first via, wherein said second end of said metal trace is at least partially externally exposed; and surrounding said electrical pathway by a biocompatible insulation material.

20. The method of claim 19 wherein the step of surrounding said electrical pathway comprises depositing alumina to surround said electrical pathway.

21. The method of claim 19 wherein the step of forming a second electrically coupled via comprises forming said second via from a biocompatible material.

22. The method of claim 19 wherein the step of forming a second electrically coupled via comprises forming said second via from platinum such that said second via is biocompatible.

23. A method of forming an electrically conductive hermetic connection to a hermetically sealed integrated circuit, said method comprising the steps of:

forming an integrated circuit on a face of a semiconductor substrate, said integrated circuit having one or more electrically conductive pads for communicating and/or providing power to said integrated circuit;

forming one or more electrical pathways for providing electrical connection to said one or more electrically conductive pads; said pathways having first ends coupled to said one or more pads and second ends exposed for external electrical connection from said sealed integrated circuit;

encapsulating said semiconductor substrate and said integrated circuit except for selected portions of said second ends of said electrical pathways; and wherein the step of forming one or more electrical pathways comprises at least in part the steps of:

forming a plurality of metal traces having first and second ends, including at least an innermost trace closest to said semiconductor substrate and an outermost trace furthest from said semiconductor substrate, each adjacent pair of metal traces separated by an insulating material sandwiched in-between so as to form a hermetic seal between said metal traces;

forming at least one interconnection via surrounded by said insulating material for interconnecting said adjacent pairs of metal traces;

forming at least one innermost via for interconnecting said innermost trace to at least one of said pads on said integrated circuit;

depositing an insulating material for encapsulating said plurality of metal traces, said integrated circuit and said semiconductor substrate;

enabling at least a portion of one said second end of an outermost metal trace to be partially externally exposed through the encapsulating insulating material for external communication; and wherein said combination of metal traces, sandwiched insulating material, encapsulating material and vias provides a hermetic communication path to said integrated circuit from a location external to said implantable package.

* * * * *